US009880099B2

United States Patent
Parker

(10) Patent No.: US 9,880,099 B2
(45) Date of Patent: Jan. 30, 2018

(54) SCANNER FOR SPATIALLY OFFSET RAMAN SPECTROSCOPY

(71) Applicant: COBALT LIGHT SYSTEMS LIMITED, Oxfordshire (GB)

(72) Inventor: William Parker, Oxfordshire (GB)

(73) Assignee: Agilent Technologies LDA UK Limited, Cheshire (GB)

( * ) Notice: Subject to any disclaimer, the term of this patent is extended or adjusted under 35 U.S.C. 154(b) by 28 days.

(21) Appl. No.: 15/200,540

(22) Filed: Jul. 1, 2016

(65) Prior Publication Data

US 2017/0003226 A1 Jan. 5, 2017

(30) Foreign Application Priority Data

Jul. 3, 2015 (GB) .................................. 1511696.5

(51) Int. Cl.
*G01J 3/44* (2006.01)
*G01N 21/65* (2006.01)
*G01N 21/85* (2006.01)
*G01N 21/90* (2006.01)

(52) U.S. Cl.
CPC ............ *G01N 21/65* (2013.01); *G01N 21/85* (2013.01); *G01N 21/90* (2013.01); *G01N 2201/1056* (2013.01)

(58) Field of Classification Search
CPC ........ G01N 21/65; G01N 21/85; G01N 21/90; G01N 2201/1056; G01J 3/44; G01J 3/2889
USPC .......................................................... 356/301
See application file for complete search history.

(56) References Cited

U.S. PATENT DOCUMENTS

2005/0094006 A1* 5/2005 Silverstein ............ G06T 3/4015
                                                          348/272
2015/0131091 A1    5/2015 Smith

FOREIGN PATENT DOCUMENTS

| EP | 0 633 541 | 1/1995 |
|----|-----------|--------|
| WO | WO 2006/061565 | 6/2006 |
| WO | WO 2006/061566 | 6/2006 |
| WO | WO 2012/149343 | 11/2012 |

OTHER PUBLICATIONS

Matousek et al., Applied Spectroscopy, vol. 59, No. 4, 2005 "Subsurface Probing in Diffusely Scattering Media Using Spatially Offset Raman Spectroscopy".
Loeffen et al., Proc. SPIE 8018, Chemical, Biological, Radiological, Nuclear and Explosives (CBRNE) Sensing XII, 80181E (Jun. 3, 2011), "Chemical and explosives point detection through opaque containers using spatially offset Raman spectroscopy (SORS)".
A Frisby et al., Proc. Of SPIE vol. 8189 81890B-1 Spatially offset Raman spectroscopy (SORS) for through-barrier proximal chemical and explosive detection (Oct. 26, 2011).

* cited by examiner

*Primary Examiner* — Hina F Ayub
(74) *Attorney, Agent, or Firm* — Leason Ellis LLP

(57) ABSTRACT

Apparatus for carrying out spatially offset Raman spectroscopy (SORS) is described. The apparatus comprises a rotatable prism arranged such that a spatial offset between an entry region and a collection region at a sample is dependent upon an angle of rotation of the prism.

22 Claims, 2 Drawing Sheets

SCANNER FOR SPATIALLY OFFSET RAMAN SPECTROSCOPY

CROSS REFERENCE TO RELATED APPLICATIONS

This application claims the benefit of priority under 35 U.S.C. Sec. 119 of United Kingdom Application No. 1511696.5 filed Jul. 3, 2016 which is hereby incorporated by reference as if set forth in its entirety herein.

The present invention relates to apparatus and methods for carrying out spatially offset Raman spectroscopy, for example a scanner unit for this purpose, and a method of operating such a scanner unit.

INTRODUCTION

Spatially offset Raman spectroscopy is described in a number of prior art publications such as Matousek et al., Applied Spectroscopy, Volume 59, Number 4, 2005. The technique is used to retrieve Raman spectra of subsurface layers of a sample, for example in diffusely scattering media. The technique is based on delivering probe light to one or more entry surface regions of a sample, and collecting scattered probe light from one or more collection surface regions that are laterally spaced from the entry region(s). Raman spectral features are then identified in the collected light. The depth profile of the Raman scattering which gives rise to the Raman spectral features in the collected light is then dependent on the lateral spacing. A single spacing between entry and collection can be used, or data from multiple spacings can be used to provide more accurate depth based information.

The technique is discussed extensively in WO2006/061565 and WO2006/061566, the contents of which are incorporated herein in their entirety for all purposes. Typically, the probe light may be delivered as a laser beam to form a laser spot on the sample surface thereby defining an entry surface region, and the collection region may be defined by collection optics arranged to collect the backscattered light.

The technique may be used with samples comprising highly scattering materials such as powders, turbid liquids, opaque plastics and glass materials, paper and cardboard materials, and with samples comprising weakly scattering materials such as weakly scattering and transparent liquids, transparent and coloured plastics and glasses, and so forth. Samples can comprise layers of such materials, such as a pharmaceutical tablet within a white plastic blister pack, a liquid in a glass or plastic bottle, a granulated material in a paper sack, and so forth, and in such cases, the technique can be very useful in determining Raman spectral features of the contained material while suppressing the signature of the container or packaging.

Equipment for carrying out spatially offset Raman spectroscopy is sold in various forms, but a need continues for providing compact and robust equipment that is able to derive more reliable and repeatable Raman spectral features from a range of sample types and configurations.

SUMMARY OF THE INVENTION

Accordingly, the invention provides apparatus for carrying out spatially offset Raman spectroscopy on a sample, comprising: a light source arranged to form a beam of probe light directed along an optical path to an entry region on the sample; collection optics arranged to receive said probe light from a collection region on the sample following subsurface scattering of said probe light within the sample; a spectral analyser arranged to detect Raman scattering spectral features in the probe light received through the collection optics; and a rotatable prism disposed in the optical path, the rotatable prism being arranged such that a spatial offset between the entry region and the collection region is dependent upon the angle of rotation of the prism.

The apparatus may be provided as a scanner unit, for example such a scanner unit for handheld use. In any case, the use of a rotatable prism to control the spatial offset between the entry and collection regions enables a compact and reliable apparatus to be constructed.

In particular, the probe light beam may be directed through opposing faces of the prism, for example parallel or substantially parallel faces of such a prism. To this end, a square prism may conveniently be used, but other trapezoidal, rectangular and other forms may be used. In any case, the prism may be configured and arranged such that the probe light beam arriving at the sample is aligned in substantially the same direction relative to the apparatus regardless of the spatial offset of the entry region and corresponding rotational position of the prism. In other words, the apparatus may be arranged such that the angle between the beam of probe light arriving at the sample, and an optical axis of the collection optics, is independent of one or both of the angle of rotation of the prism and the spatial offset. Similarly, the apparatus may be arranged such that the angle of incidence of the probe beam at the sample is independent of the spatial offset between the entry region and the collection region at the sample.

Such arrangements provide more consistent levels of illumination of the sample, by minimising variations in surface reflection and penetration into subsurface portions of the sample, thereby improving consistency in the relationship between spectral features determined for different spatial offsets.

Although the prism may have substantially parallel opposing faces, other forms of prism may be used, for example a prism having non parallel opposing faces, non flat faces and so forth. For example, a wedge prism may be used which provides reorientation of the probe light beam and therefore added flexibility in designing the apparatus in a compact form, and may also be used to provide anamorphic beam shaping. Translation of a wedge prism could also be used to control the spatial offset, instead of or as well as by rotation of the prism. A curved prism face, for example a cylindrical or other curve, may be used to create a change in focus and spot size for one lateral axis of the beam, such that entry region spot shape and size can be controlled. Such a curved face could be used to provide a different optical lensing effect at different spatial offsets, for example between zero or null offset and other offset orientations.

Typically, the apparatus may be arranged to provide rotation of the prism over a range of less than ninety degrees, to thereby provide a corresponding range of spatial offsets between the entry region and the collection region. Typically, a maximum spatial offset between the entry and collection regions provided by the apparatus may be in the range of 5 mm to 25 mm. The minimum spatial offset which is useful for detecting and/or isolating sub-surface scattering may be as small as 1 mm or less. Typically, to detect such sub-surface scattering, the offset between the entry and collection regions should be more than about half the width of the entry region, as determined by the width of the probe light beam arriving at the sample.

The apparatus may also be arranged such that rotation of the prism gives rise to a negative spatial offset in an opposite direction to the direction of the maximum spatial offset. The apparatus is preferably also arranged such that a particular rotational position of the prism gives rise to a minimum spatial offset of zero mm between the entry region and the collection region, i.e. in which the entry and collection regions are coincident.

It should be noted that, although entry and collection regions may typically be circular or ellipsoidal, being defined by the optics used to generate the regions, other shapes and structures of regions may be used, including regions made up of a plurality of discrete and separate areas, regions including rings and loops, and so forth, and the term spatial offset should be understood accordingly, as a relative positioning of the regions which may or may not include a clearly defined zero or null offset where the regions are coincident. The collection region may typically be elongated due to input characteristics of the spectral analyser, for example if the spectral analyser comprises a spectrometer having an input slit. If the collection region is elongate then the apparatus may also be arranged such that the entry region is elongate along a parallel axis to the elongation of the collection region, to help maximise collected signal at one or both of null and non null spatial offsets.

In order to control rotation of the prism and therefore the spatial offset, the apparatus may further comprise an actuator arranged to control rotation of the prism. The apparatus may then be arranged, for each spatial offset, to receive said probe light from the sample, and to separately detect Raman scattering spectral features for each such spatial offset. The apparatus may then be arranged to combine the detected Raman scattering spectral features for each of the plurality of different spatial offsets to preferentially select for depth or a range of depths within the sample. The apparatus may also be arranged to derive characteristics of a sub-surface region of the sample from the detected Raman scattering spectral features, for example by identifying one or more chemical components of one or more sub-surface regions, for example identifying such characteristics as profiles of depth within the sample. Such functionality may be carried out by a control unit, an analyser, or other component of the apparatus.

The invention also provides methods corresponding to the above apparatus, for example methods for carrying out spatially offset Raman spectroscopy, for example comprising providing a rotatable prism in an optical path between a light source and a sample, the light source providing a beam of probe light, and rotating said prism to different positions, such that the beam of probe light is delivered to each of a plurality of entry regions on a sample, each entry region corresponding to a different prism position. Said probe light may then be received from a collection region on the sample, each entry region being at a different spatial offset from the collection region so that Raman scattering spectral features can be detected in the received probe light, separately for each spatial offset.

The method may further comprise combining the detected spectral features from the different spatial offsets to preferentially select for a particular depth or range of depths within the sample. Characteristic of a sub-surface region of the sample may then be derived from the detected Raman spectral features for the different spatial offsets. Detected spectral features from different offsets may be combined in such ways using a control unit forming part of a scanner unit carrying out the method, and results of the analysis may be presented on a display of such a scanner unit.

BRIEF DESCRIPTION OF THE DRAWINGS

Embodiments of the invention will now be described, by way of example only, with reference to the accompanying drawings, of which.

DETAILED DESCRIPTION OF EMBODIMENTS

Figure 1:
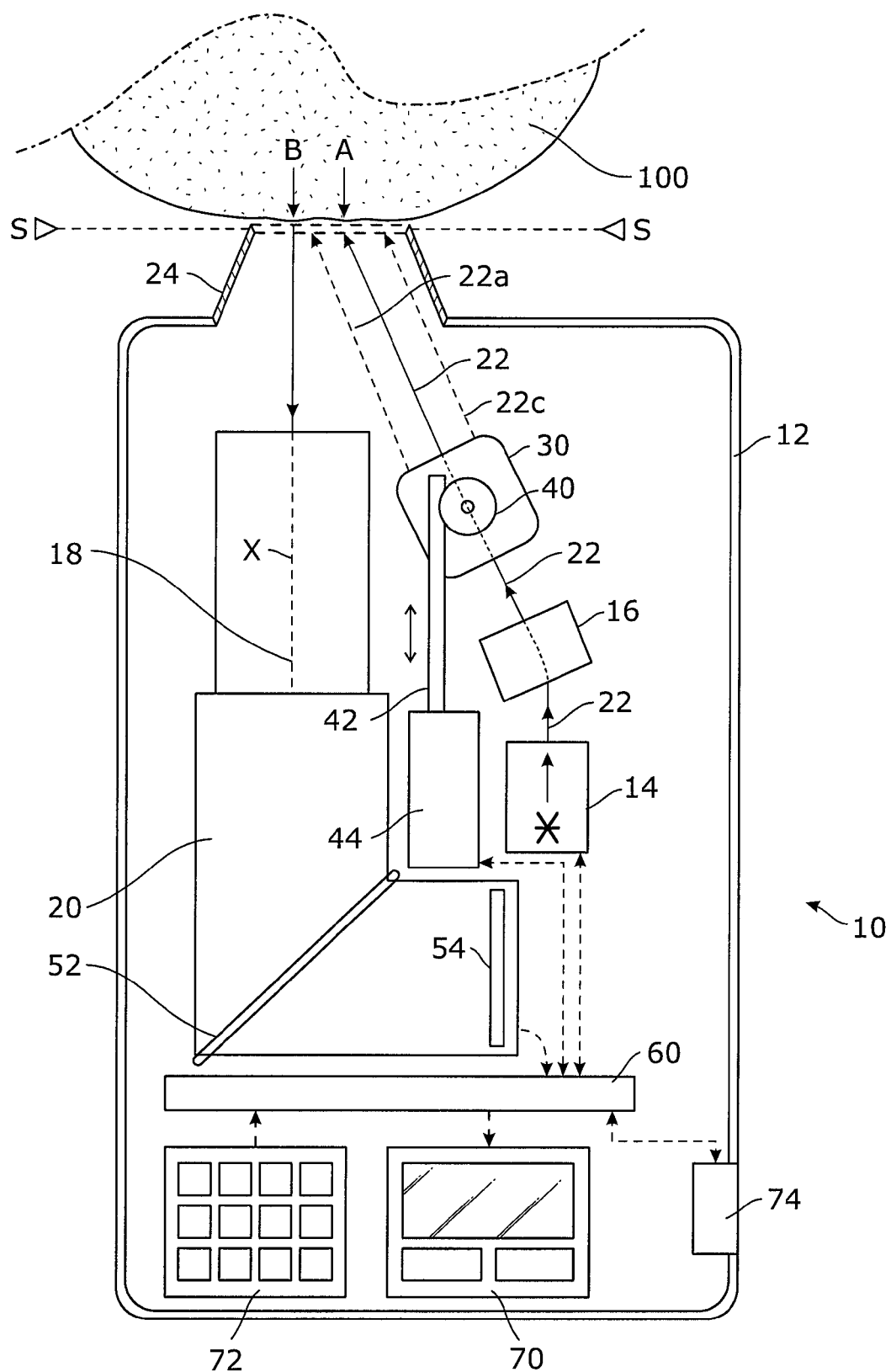
FIG. 1 shows schematically, in plan view, an apparatus for carrying out spatially offset Raman spectroscopy on a sample.

Referring now to FIG. 1 there is shown schematically, in plan view, an apparatus for carrying out spatially offset Raman spectroscopy on a sample. The apparatus may conveniently be provided as a scanner unit for handheld use. Some typical applications for such a scanner unit could be in the areas of homeland security, industrial manufacturing, agrochemicals, medicine, and so forth.

In homeland security applications the scanner unit could be used to test personal effects and luggage for illicit or dangerous substances such as explosives, narcotics, and chemical precursors of such components, with the samples to be tested being bottles, bags, tubes and other containers containing materials which potentially comprise such target substances, or various other types of sample. In the area of industrial manufacturing such a scanner unit could be used to check the composition of raw materials and final chemical products contained within drums, bottles, bags, sacks, blister packs, tablets, and so forth. In agrochemicals, samples could be, for example, sacks containing agrochemicals such as fertilisers, insecticides, and other substances. A variety of other applications for such a scanner will be apparent to the skilled person for example from the literature relating to spatially offset Raman spectroscopy.

The scanner unit 10 illustrated in FIG. 1 comprises a casing 12 within which are housed a laser sub-assembly 14, probe beam conditioning optics 16, collection optics 18, and a spectral analyser 20. The laser sub-assembly 14 comprises a laser (not shown) which generates a laser beam which constitutes a beam of probe light 22 for testing a sample 100, which could for example be a bottle, drum or other container of a liquid to be analysed, or a bag, sack or other container of a solid material to be analysed. The laser may typically be a semiconductor diode laser operating in the near infra-red, for example at 830 nm with a power of around 10 to 500 mW.

The beam of probe light 22 passes from the laser sub-assembly 14 though the probe beam conditioning optics 16 and then to the sample 100. After scattering within the sample 100, some of the probe light is collected by the collection optics 18 which passes the collected probe light to the spectral analyser 20 for detection of one or more Raman scattering spectral features in the collected probe light. The Raman scattering spectral features may then be used as an indication of chemical properties of sub surface regions of the sample, for example to identify particular chemical components and other properties of the sample.

In FIG. 1 the scanner unit 10 is held adjacent to the sample 100 by a spacer element 24 which also forms part of the scanner unit. The spacer element 24 helps ensure that the sample is held stably at a fixed and suitable position relative to the scanner unit, for example by defining a plane S within which a surface of the sample to be tested is located for scanning. The spacer element 24, which in FIG. 1 is in the form of a truncated cone, contains suitable apertures to permit the probe beam 22 to pass to the sample 100, and for probe light scattered out of the sample 100 to be collected by the collection optics 18. The probe beam conditioning optics 16 may include a defocus lens, or other suitable optical element or arrangement such as a diffuser, which causes the probe beam to be slightly divergent, thereby reducing the risk of eye damage for an operator or bystander, and which also reduces the risk of burning the sample 100. The probe beam conditioning optics 16 may also include an optical element, such as an expansion prism, a wedged prism, a diffraction grating, or a holographic element, for anamorphically expanding or otherwise altering the probe beam into a configuration more suitable for use in the spatially offset Raman spectroscopy process. At the same time, the expansion prism or other optical element can be used to turn the beam towards the sample, to help provide a more compact scanner unit layout.

In the prior art relating to spatially offset Raman spectroscopy, it is known to use a range of offsets between an entry region on the sample where the probe beam 22 is incident on the sample, and a collection region on the sample from where the collection optics collects probe light scattered within the sample. This range of offsets can be used to provide a better selection for depth within the sample, for example to help exclude Raman spectral features arising from surface layers of the sample, or to select for a particular depth or range of depths within the sample. Such techniques are described in WO2006/061565 and WO2006/061566, the contents of which are hereby incorporated by reference for all purposes, and elsewhere, for example in Loeffen et al., Proc. SPIE 8018, Chemical, Biological, Radiological, Nuclear, and Explosives (CBRNE) Sensing XII, 80181E (Jun. 3, 2011), "Chemical and explosives point detection through opaque containers using spatially offset Raman spectroscopy (SORS)". The range of offsets used in spatially offset Raman spectroscopy can be understood as a range of different distances or separations between the entry and collection regions, or between the centres of these regions, although with more complex geometries of one or both regions a simple distance may not always be an appropriate measure. Of course, some probe light reflected from the surface of the sample may be collected, especially where the entry collection regions are close together or overlap to some extent. At or close to a zero or null offset where the entry and collection regions are coincident or collocated, a majority of the collected light may result from surface scattering, but this typically still contains useful Raman spectral information for example relating to the surface of the sample. As discussed below, such surface scattering can be used to help correct spectral data from larger offsets.

In FIG. 1 the position of such a collection region is shown by arrow B. The shape of the collection region may be of various shapes and forms determined by the configuration of the collection optics 18, the spectral analyser 20, optical coupling between these elements, and other factors. With the apparatus of FIG. 1, however, the collection region may typically be an approximately circular spot with a diameter of about 1 to 3 mm, or alternatively an elongate shape about 1 to 3 mm length in the major axis with an aspect ratio of greater than 1:1, for example greater than 2:1 or greater than 10:1, and optionally up to about 40:1. In some embodiments for example, the collection region is defined by an image on the sample of a collection slit of the spectrometer. In some embodiments this image can have dimensions in the region of 1.8 mm×0.08 mm, depending on the collection optics and spectrometer slit. The apparatus (and in particular one or more of the probe beam conditioning optics 16, the prism 30, and laser 14) may then be used to form an entry region which is also elongate, with a major axis broadly aligned with the major axis of the collection region. In particular, the entry region may be formed to be of a similar shape and/or aspect ratio as the collection region, thereby maximising collected signal. In some embodiments such an arrangement may also enhance depth selection by minimising the illumination distribution, for example by forming the entry and collection regions to be elongate in a direction perpendicular to the direction of spatial offset.

The position of the collection region on the sample, relative to the scanner, is approximately fixed due to the optical axis of the collection optics X being perpendicular to the plane S of the sample surface held against the spacer element 24, although an oblique angle between X and S could be used, in which case the collection region would typically be elliptical.

The entry region in FIG. 1 is shown by arrow A. According to the invention, the optical path from the laser sub-assembly 14, as it approaches the sample 100, can be laterally offset without changing direction or angle of incidence, by rotation of a prism 30 also mounted within the housing 12. The prism is therefore located in the optical path between the laser sub-assembly 14 and the sample 100. Extreme positions of the optical path between which the probe beam can be adjusted using rotation of the prism 30 are shown in FIG. 1 as probe beam paths 22a and 22c. The collection optics 18 shown in FIG. 1 are stationary relative to the casing 12, so that by rotating the prism 30, a spatial offset at the sample surface S between the entry region A and the collection region B can be directly controlled.

The entry region formed using the apparatus of FIG. 1 will typically be elliptical, due to the oblique angle of incidence at the sample. An entry region with a diameter or dimensions in the region of 0.5 mm to 3 mm may be used. An entry region which is too small will tend to lead to burning of the sample, while a spot size which is too large reduces the degree to which the scanner is able to distinguish between different layers or depths within the sample through the offset process.

The range of spatial offsets which it would be desirable to provide in a particular scanner unit 10 may vary according to intended applications. For example, if the scanner unit is to be used with samples into which the probe light can more easily penetrate then the range of spacings may be increased to take advantage of this and the availability of greater depth range for the spatially offset Raman spectroscopy process. However, typically the scanner may provide a range of offsets of the order of 0 mm to 10 mm, perhaps as much as to 20 mm, 25 mm or more. Defined in terms of the size of the range of offsets, or in terms of the size of the lateral range of displacement of the beam provided by the movement of the prism, for example measured proximal to the prism or where the beam exits the apparatus, this may be, for example, one of: at least 10 mm, at least 20 mm, or at least 30 mm, and this range includes the position of a null or zero offset if provided, and any negative offset if provided for by the apparatus. A small negative offset may be provided at the supposed plane of the sample S, for example with an offset range of minus 2 mm to plus 10 mm, to thereby provided for an actual zero offset when the sample is slightly misplaced towards the scanner unit than the intended sample plane S.

Figure 2A:
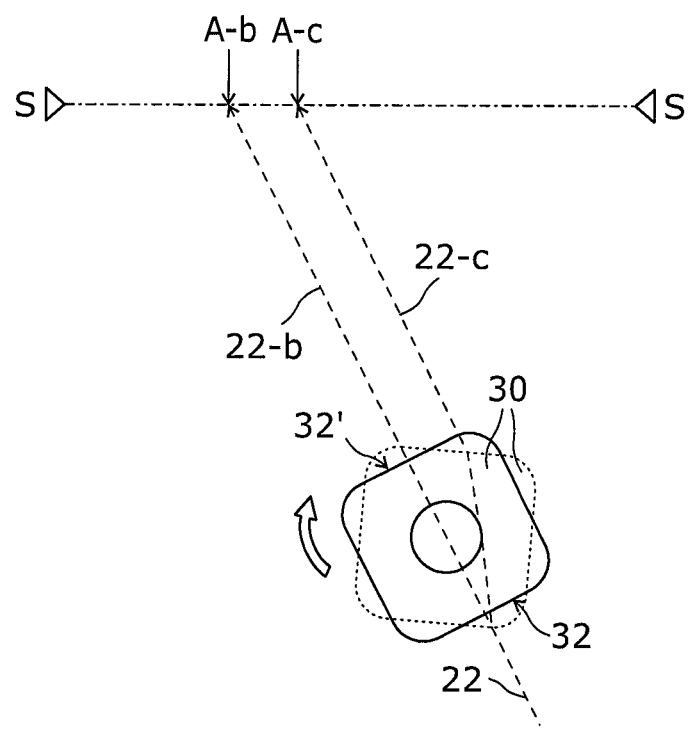
FIGS. 2a and 2b show how rotation of the prism of FIG. 1 gives rise to variations in spatial offset between the entry and collection regions on the surface of the sample.
Figure 2B:
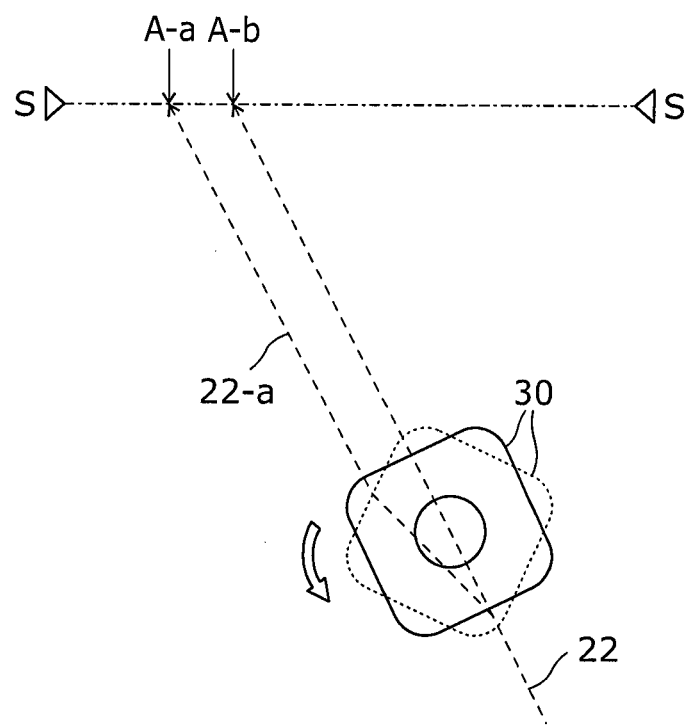

The process of varying the entry region offset using the prism 30 is illustrated further in FIGS. 2a and 2b, which for clarity show just the prism 30 with the related optical paths of the probe beam 22 and the geometrical construct of the sample surface S under different rotations of the prism 30. The prism 30 of FIGS. 2a and 2b comprises opposing first and second faces 32 and 32'. When these faces are perpendicular to the incoming probe light beam 22 (as shown by the prism position depicted in solid lines in both figures), the beam passes through the prism without deviation or offset, and emerges along probe beam path 22-b, to form an entry region on the sample at A-b. When the prism is rotated such that the faces 32 and 32' are no longer perpendicular to the incoming probe light beam 22, the beam passes through the prism with a deviation, or offset. In FIG. 2a, the prism rotation is clockwise from the point of view of the observer, and therefore the beam 22 emerges along an offset probe beam path 22-c, which is to the right of and parallel to undeviated path 22-b, to form an entry region on the sample at A-c which is more distant from the collection region B than A-b.

Rotation in the opposite direction, illustrated in FIG. 2b, causes an offset in the opposite direction as probe beam path 22-a, to form an entry region on the sample at A-a which is closer to the collection region B, and indeed which may be coincident with the collection region B to provide a zero offset position. For a "negative offset" discussed above, the entry region A-a may lie beyond the collection region B, so that the zero offset position would then be located between A-a and A-b. The zero offset position is effectively a coincidence between an entry region A-a and the collection region B, for example to provide a zero-offset condition useful for analysis and/or calibration of the spatially offset Raman spectroscopy results.

The prism depicted in FIGS. 1, 2a and 2b is a square prism, although since only the opposing faces 32 and 32' are used in this example for directing the probe beam 22, a square form is not strictly necessary. Of course, it would be possible to use all four faces of the square prism, or some other prism arrangement, for example to provide a prism which rotated continuously to provide a repeated scanning effect. Such an arrangement could also be used to move more rapidly between extremes of spatial offset such as A-a and A-c in FIGS. 2a and 2b. The transition of the beam across one or two corners of the prism provides the rapid transition between the extreme positions of spatial offset. The size and refractive index of the prism can be chosen according to particular need and design for a particular scanner unit. In one example, a square prism with sides of length 17 mm and refractive index n=1.763 at 830 nm is used (for example N-SF11 glass), giving a lateral beam offset of about 5.8 mm in each direction for a prism rotation of 40 degrees in each direction, so a range of offset of about 11.6 mm overall. A glass of lower refractive index provides a smaller range of offsets for the same prism size (N-BK7 glass with n=1.5102 at 830 nm provides an offset range of about 9.7 mm), and a glass of higher refractive index provides a larger range of offsets for the same prism size (N-LASF79 glass with n=1.9776 at 830 nm provides an offset range of about 13 mm). In designing a particular scanner unit, the space available for a larger prism, the increased weight of a larger prism and/or heavier glass of higher refractive index, and the costs of different prisms and glass types, may be taken into account.

To provide space in the scanner for accommodating the various optical components, while providing a suitable offset between the entry and collection regions in a range of about 0 mm to 20 mm, it will typically be desirable for the optical axis X of the collection optics and the angle of incidence of the probe light beam 22 at the sample to be non-parallel. In the figures, the optical axis of the collection optics X is perpendicular to the sample plane S, while the probe light beam 22 is incident at the sample plane S at an oblique angle, but the converse arrangement could be used in which the axis X is oblique and the probe beam 22 is perpendicular could be used, or both could be oblique. In the arrangement shown in the figures the probe beam arrives at the sample plane S at an angle from about 15 and 45 degrees, or more preferably from about 20 to 40 degrees, although other angles could be used, for example in the range from about zero to 45 degrees. In particular, a zero angle could be used in designs where the delivery and collection paths to and from the sample from the apparatus are coincident or overlapping or coaxial, for example when a common lens is used for both delivery and collection.

In the figures, the axis of rotation of the prism is depicted as generally perpendicular to the plane of the figure and perpendicular to the direction of both the probe beam 22 approaching the sample and the optical axis X, but this is not a requirement in order to provide suitable offset of the probe beam using the prism 30.

The use of a prism 30 as described herein to effect offset of the probe beam without substantial change of direction enables the scanner unit to direct the probe beam to the sample at the same angle of incidence for all offset spacings, or subject to possible slight variations in the sample surface over the offset range, at least at the same angle relative to the optical axis X. Since reflection of probe light from the sample, and penetration of the probe light into the sample will typically vary according to angle of incidence and/or angle relative to X, both due to direction and shape of the entry region, and the behaviour of the probe light in terms of scattering into the collection region and on to the collection optics will also typically vary according to angle of incidence at the entry region, using a prism 30 in this way provides a more consistent instrument. The use of the prism as described also provides a compact arrangement which is robust to rough handling of the scanner unit, such as being dropped or knocked.

Controlled rotation of the prism 30 may be effected in various different ways. In FIG. 1, the prism 30 is coupled to a co-rotating pinion 40, and a rack 42 is provided to couple linear motion from an electrical actuator 44 to rotation of the pinion. This arrangement enables the actuator to be spaced from the prism to help form a more compact scanner unit, but clearly other arrangements to drive rotation of the prism 30 may be used. For example, the electrical actuator 44 may provide rotational motion to the prism without using a linear motion arrangement, for example using a motor providing rotational motion coupled to the prism 30 using gears or by a direct coupling.

The spectral analyser 20 may be provided in various ways, with the objective of detecting Raman spectral features in the collected light. In the arrangement of FIG. 1 a spectrometer is used. This could be a dispersive spectrometer using a diffraction grating 52 such as a transmission grating, in combination with a detector such as an imaging detector 54, for example a 2D FFT-CCD array. However, other forms of spectrometer, including arrangements using one or more band pass filters selected for particular spectral features or regions of interest, could be used. If desired, the spectrometer could be coupled to the collection optics using a fibre optic bundle, to thereby better image the collected light onto the spectrometer slit and improve collection efficiency.

The scanner unit 10 may be controlled using an electronic control unit 60 comprising electronics to control the laser sub-assembly 14 and the electrical actuator 44, and to receive and analyse spectral data from the spectral analyser 20. The control unit may also receive signals from the laser sub-assembly 14 (for example relating to tuning or temperature of the laser), the electrical actuator (for example relating to position of the actuator or other control feedback), and may also provide control signals to the spectral analyser 20. The control unit 60 will typically comprise one or more microprocessors and associated memory, as well as interface electronics such as A/D and D/A converters as required.

Regarding control of the electrical actuator 44 to control of rotation of the prism 30 and therefore control offset of the probe beam 22, this may be effected by the control unit 60 according to various requirements. For example, when testing a particular sample, the control unit 60 may first of all set the offset between the entry and collection regions to be zero, so that the regions are coincident, and collect spectral data at that offset, before moving to a series of one, two or more different offsets (for example at 4 mm, 8 mm and 12 mm), collecting spectral data at each such offset. The spectral data from the various offsets can then be combined, compared or otherwise analysed by the control unit 60, in order to generate an output for display to a user of the scanner unit. Such an output could, for example, identify or confirm the presence or absence of one or more chemical components in the sample. If required, such outputs may be provided as profiles of depth within the sample for example as discussed further below.

The scanner unit 10 preferably therefore also comprises a visual display unit 70 for presenting such outputs and other control and operational information to a user, a user input unit 72 such as a keypad (which could be provided as a touch sensitive function of the visual display unit) to enable a user to provide inputs and other controls to the unit (for example selection of particular scanning programs, sensitivities etc.), and a wired and/or wireless interface 74 for digital communication with the scanner unit, for example to update firmware, download spectral data and other results, and so forth.

Use of Raman spectral data obtained from different spatial offsets between the collection and entry regions in order to determine subsurface characteristics of a sample is described in the WO2006/061565 and WO2006/061566 documents mentioned above, and the data and spectral processing techniques described therein are hereby incorporated by reference. For example, it should be noted that spectral data for each spatial offset are collected separately. Typically this is achieved by using each different spatial offset during a separate time interval, in the present case through appropriate positioning of the rotatable prism, and separately collecting and carrying out spectral detection of the Raman scattered light for each such offset, although other techniques could be used.

Since each spatial offset gives rise to a different depth profile of Raman scattering resulting in the collected light, the spectral features for the different spatial offsets can be combined to select for a particular depth or range of depths within the sample. Techniques for achieving this which are described in WO2006/061565 and WO2006/061566 typically involve deriving characteristics of a sub-surface region of the sample from changes in intensities of one or more Raman spectral features between different spatial offsets. Techniques include subtraction of spectra or spectral features for different spacings, for example in which a spectrum at a zero or small spatial offset is subtracted from a spectrum at a larger spatial offset, in order to reduce the contribution from surface layers in the resulting spectrum. Other techniques include multivariate data analysis, such as principle component analysis in order to estimate a contribution to the observed spectral data which arises from a particular depth, range or profile of depths within the sample. The subtraction technique may be used with just two spatial offsets, for example a zero or small offset, and a larger offset. The multivariate techniques typically require spectral features from a larger number of offsets to be combined to be effective, for example around ten different offsets.

Such techniques enable the scanner to combine the detected spectral features for each of a plurality of different spatial offsets to preferentially select for depth or a range or profile of depths within the sample.

In some cases it may be appropriate to collect scattered light from just one spatial offset, and to derive characteristics of the sample using only this offset, for example where the expected properties or Raman spectral characteristics of a container forming a surface of the sample are already known, or the Raman spectral characteristics of such a container are small or can be accounted for in other ways, for example through spectral separation or analysis.

These and similar techniques may be carried out by the control unit 60, or externally to the scanner 10. Results of such analysis, for example identifying the presence or concentration of one or more particular chemical substances in the sample, may then be presented on the display 70.

Although particular embodiments of the invention have been described, it will be apparent to the skilled person that various modifications and alterations can be made without departing from the scope of the invention.

For example although the arrangements described above use non-parallel and separated paths for delivery of probe light to the sample and collection of backscattered light for passing to the spectral analyser, the delivery and collection paths between the apparatus and the sample could be coincident or at least parallel and/or overlapping and/or coaxial. For example if a common lens is used for both delivery and collection of the probe light, and such a common lens could form part of or all of the described collection optics 18. Using common optics for the delivery and collection paths may be advantageous if a zero or small angle of incidence of the probe light beam onto the sample is required.

Similarly, although FIG. 1 shows a probe light beam being delivered to the surface of the sample at an oblique angle, and the collection optics having an axis perpendicular to the sample surface, both could be oblique, the probe light beam could be perpendicular and the collection axis oblique, or various other options and combinations.

FIG. 1 shows a spacer element 24 being used to hold the sample at a fixed position relative to the scanner while scanning takes place, this spacer element 24 could be removable so that the scanner unit can be used with or without the spacer element 24, or omitted altogether. Scanning the sample without any such spacer unit being used may be advantageous where contact with the sample is not desired, for example if scanning suspected explosives, or materials likely to adhere or stick to or otherwise damage or compromise the scanner unit.

The invention claimed is:

1. Apparatus for carrying out spatially offset Raman spectroscopy on a sample, comprising:
   a light source arranged to form a beam of probe light directed along an optical path to an entry region on the sample;
   collection optics arranged to receive said probe light from a collection region on the sample following subsurface scattering of said probe light within the sample;

a spectral analyser arranged to detect Raman scattering spectral features in the probe light received through the collection optics; and a rotatable prism disposed in the optical path, the rotatable prism being arranged such that a spatial offset between the entry region and the collection region is dependent upon the angle of rotation of the prism.

2. The apparatus of claim 1 wherein the prism comprises opposing faces, and the apparatus is arranged such that the probe beam enters and exits the rotatable prism through the opposing faces.

3. The apparatus of claim 2 wherein the opposing faces are substantially parallel.

4. The apparatus of claim 3 wherein the prism is a square prism.

5. The apparatus of claim 1 arranged to provide rotation of the prism over a range of less than ninety degrees thereby providing a corresponding range of spatial offsets between the entry region and the collection region.

6. The apparatus claim 1 arranged such that the angle between the beam of probe light arriving at the sample, and an optical axis of the collection optics, is independent of one or both of the angle of rotation of the prism and the spatial offset.

7. The apparatus of claim 6 wherein the angle between the beam of probe light arriving at the sample, and an optical axis of the collection optics, is in the range of 15 to 45 degrees.

8. The apparatus of claim 1 arranged such that the angle of incidence of the probe beam at the sample is independent of the spatial offset between the entry region and the collection region at the sample.

9. The apparatus of claim 1 further comprising an actuator arranged to control rotation of the prism so as to vary the spatial offset between the entry region and the collection region.

10. The apparatus of claim 9 arranged such that rotation of the prism gives rise to a maximum spatial offset of between 5 mm and 25 mm between the entry region and the collection region.

11. The apparatus of claim 10 arranged such that rotation of the prism gives rise to a negative spatial offset in an opposite direction to the direction of the maximum spatial offset.

12. The apparatus of claim 9 arranged such that rotation of the prism gives rise to a minimum spatial offset of zero between the entry region and the collection region.

13. The apparatus of claim 1 further arranged to control rotation of the prism to receive said probe light from the sample for a plurality of different spatial offsets and to separately detect Raman scattering spectral features for each such spatial offset.

14. The apparatus of claim 13 further arranged to combine the detected Raman scattering spectral features for each of the plurality of different spatial offsets to preferentially select for depth or a range of depths within the sample.

15. The apparatus of claim 1, wherein the apparatus is arranged to derive characteristics of a sub-surface region of the sample from the detected Raman scattering spectral features.

16. A method of carrying out spatially offset Raman spectroscopy, comprising:

providing a rotatable prism in an optical path between a light source and a sample, the light source providing a beam of probe light;

rotating said prism to different positions, such that the beam of probe light is delivered to each of a plurality of entry regions on a sample, each entry region corresponding to a different prism position;

receiving said probe light from a collection region on the sample, each entry region being at a different spatial offset from the collection region; and detecting, for each said spatial offset, Raman scattering spectral features in the received probe light.

17. The method of claim 16 wherein the probe light is received from the collection region on the sample following subsurface scattering within the sample.

18. The method of claim 16 wherein, for each entry region, the beam of probe light arriving at the sample is substantially parallel to the probe beam for each other entry region.

19. The method of claim 16 wherein the prism comprises opposing parallel faces, and for each position of the prism, the beam of probe light passes through the opposing parallel faces.

20. The method of claim 16 further comprising combining the detected spectral features from the different spatial offsets to preferentially select for a particular depth or range of depths within the sample.

21. The method of claim 16 further comprising detecting one or more characteristics of a sub-surface region of the sample from the detected Raman spectral features for the different spatial offsets.

22. The method of claim 21 wherein detecting one or more characteristics comprises identifying one or more chemical components of a sub-surface region of the sample.

* * * * *